(12) United States Patent
Cordi et al.

(10) Patent No.: US 6,172,097 B1
(45) Date of Patent: Jan. 9, 2001

(54) SPIRO IMIDAZOLINE COMPOUNDS

(75) Inventors: Alex Cordi, Suresnes; Mark Millan; Adrian Newman-Tancredi, both of le Pecq; Mauricette Brocco, Paris, all of (FR)

(73) Assignee: Adir et Compagnie, Courbevoie (FR)

( * ) Notice: Under 35 U.S.C. 154(b), the term of this patent shall be extended for 0 days.

(21) Appl. No.: 09/465,619

(22) Filed: Dec. 17, 1999

(30) Foreign Application Priority Data

Dec. 18, 1998 (FR) .................................. 98 16000

(51) Int. Cl.$^7$ ..................... A61K 31/4184; C07D 235/02
(52) U.S. Cl. ........................ 514/396; 514/400; 548/301.1
(58) Field of Search .................................. 514/396, 400; 548/301.1

(56) References Cited

U.S. PATENT DOCUMENTS 5,648,374 * 7/1997 Cordi et al. ........................ 514/401
5,670,646 * 9/1997 Worley et al. ..................... 548/301.1

* cited by examiner

*Primary Examiner*—Robert W. Ramsuer
*Assistant Examiner*—Donya N Wright
(74) *Attorney, Agent, or Firm*—The Firm of Hueschen and Sage

(57) ABSTRACT

The invention relates to a compound of formula (I):

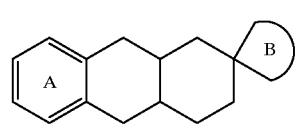

(I)

wherein:
A represents an optionally substituted benzene ring,
B represents an imidazoline ring of formula (Ia) or (Ib):

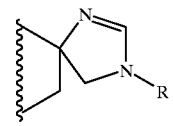

(Ia)

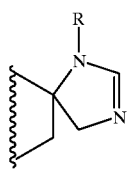

(Ib)

and medicinal products containing the same/are useful in treating or in preventing depression, obesity, panic attacks, anxiety, obsessive-compulsive disorders, cognitive disorders, phobias, impulsive disorders associated with the abuse of drugs and withdrawal therefrom, sexual dysfunctions, and Parkinson's disease.

11 Claims, No Drawings

SPIRO IMIDAZOLINE COMPOUNDS

FIELD OF THE INVENTION

The present invention relates to new Spiro imidazoline compounds, and to their use as α2-adrenergic antagonists and monoamine reuptake blockers.

DESCRIPTION OF THE PRIOR ART AND BACKGROUND OF THE INVENTION

The adrenergic nervous system plays an important role at a number of levels, for example at arterial, venous, cardiac and renal level, and at the level of the central and peripheral autonomic nervous systems. Compounds capable of interacting with adrenergic receptors can thus induce a large number of physiological responses, such as vasoconstriction, vasodilation, an increase or decrease in cardiac rhythm, variation in the strength of contraction of the cardiac muscle and variation in metabolic activities. Various adrenergic compounds have been used in the past to modify these or other physiological responses.

Spiro imidazoline compounds for use as α1- or α2-adrenergic agonists or partial agonists are found in the prior art (EP 635 495, EP 635 496, EP 635 497).

In addition to the fact that the compounds described in the present invention are new, they have an α2-adrenergic antagonist and monoamine reuptake-blocking profile, rendering them of use in the treatment of depression (Drug News & Perspectives, 4 (4), 1991). The main problem posed by antidepressants is that they take a long time to become effective, associated with their particular manner of action. Studies have demonstrated that the association of an α2-adrenergic antagonist with an inhibitor of monoamine (serotonin and/or noradrenaline) reuptake made it possible to reduce that length of time (Commun. Psychopharmacol, 4, pp. 95–100, 1980). The combination of those two effects in a single compound could give rise to a new generation of much more effective antidepressants. Among those compounds, napamezole (U.S. Pat. No. 5,017,584) is described as having both an α2-adrenergic antagonist activity and a monoamine reuptake-blocking activity.

DETAILED DESCRIPTION OF THE INVENTION

The compounds of the present invention, which have a new structure, have a selective α2-adrenergic antagonist profile and at the same time the ability to inhibit monoamine reuptake.

The present invention relates more especially to compounds of formula (I):

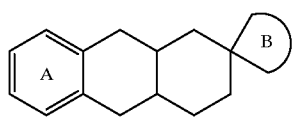

wherein:
A represents a benzene ring unsubstituted or substituted by from 1 to 4 identical or different groups selected from linear or branched $(C_1-C_6)$alkyl, linear or branched $(C_1-C_6)$alkoxy, hydroxy, polyhalo-$(C_1-C_6)$alkyl in which the alkyl moiety is linear or branched, cyano, nitro, amino, alkylamino, dialkylamino, thioalkyl, sulphonylalkyl, sulphinylalkyl, carboxy, alkoxycarbonyl, alkylcarbonyloxy, formyl, carbamoyl, carboxamide, phenyl, benzyl, and halogen atoms, B represents an imidazoline ring as represented in formulae (Ia) and (Ib):

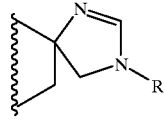

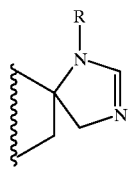

wherein R represents a hydrogen atom, a linear or branched $(C_1-C_6)$alkyl group, or a benzyl group,
it being understood that "alkyl" is understood to mean a linear or branched $(C_1-C_6)$alkyl group, their tautomers, enantiomers and diastereoisomers, and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

The preferred compounds of the invention are those wherein R represents a hydrogen atom.

Advantageously the invention relates to compounds of formula (I) wherein B represents a ring of formula (Ia).

Preferably, the invention relates to compounds of formula (I) wherein A is unsubstituted.

When the ring A is substituted by from 1 to 4 identical or different groups, the preferred substituents are linear or branched $(C_1-C_6)$alkyl, linear or branched $(C_1-C_6)$alkoxy, hydroxy, polyhalo-$(C_1-C_6)$alkyl in which the alkyl moiety is linear or branched, and halogen atoms.

Very advantageously, the invention relates to compounds of formula (I) having a trans ring junction.

More especially still, the invention relates to spiro[(1,3-diazacyclopent-1-ene)-5:2'-(trans-1',2',3',4',4'a,9',9'a,10'-octahydroanthracene)] and, preferably, to the mixture composed of spiro[(1,3-diazacyclopent-1-ene)-5:2'(S)-(trans-1', 2',3',4',4'a(R),9',9'a(S),10'-octahydroanthracene)] and its enantiomer, and to the mixture composed of spiro[(1,3-diazacyclopent- 1-ene)-5:2'(S)-(trans-1',2',3',4',4'a(S),9',9'a (R),10'-octahydroanthracene)] and its enantiomer.

The tautomers, enantiomers and diastereoisomers and addition salts with a pharmaceutically acceptable acid or base of the preferred compounds of the invention form an integral part of the invention.

The invention relates also to a process for the preparation of compounds of formula (I) characterised in that there is used as starting material a compound of formula (II):

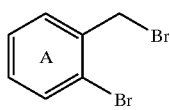  (II)

wherein A is as defined hereinbefore, which is condensed with 1,4-cyclohexanedione monoethylene acetal enolate in order to obtain a compound of formula (III):

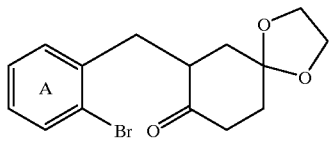  (III)

wherein A is as defined hereinbefore, which is subjected to the action of methyl(triphenyl) phosphonium iodide to yield a compound of formula (IV):

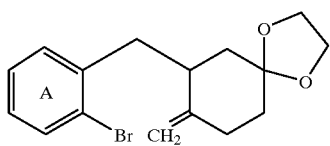  (IV)

wherein A is as defined hereinbefore, which is cyclised in the presence of tributyltin hydride and AIBN to yield a compound of formula (V):

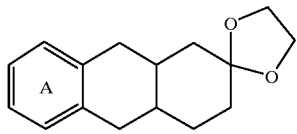  (V)

wherein A is as defined hereinbefore which is subjected, in succession, to the action of an acidic medium followed by a Strecker reaction to obtain a compound of formula (VI):

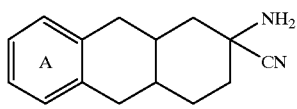  (VI)

wherein A is as defined hereinbefore, which is subjected to the action of a reducing agent, such as LiAlH$_4$ for example, to yield a compound of formula (VII):

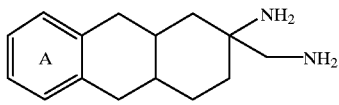  (VII)

wherein A is as defined hereinbefore which is reacted with formamidine acetate to obtain a compound of formula (I/a), a particular case of the compounds of formula (I):

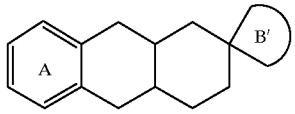  (I/a)

wherein A is as defined hereinbefore and B' represents an unsubstituted imidazoline ring as represented in formulae (Ia/a) and (Ib/a):

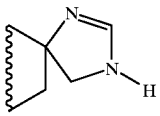  (Ia/a)

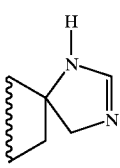  (Ib/a)

which may be subjected, in the presence of a base, to the action of a compound of formula (VIII):

R'-J  (VIII)

wherein R' represents a linear or branched (C$_1$–C$_6$)alkyl group or a benzyl group and J represents a leaving group, such as a halogen atom or a tosyl group, to yield a compound formula (I/b), a particular case of the compounds of formula (I):

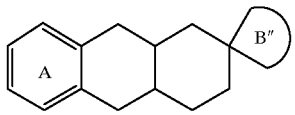  (I/b)

wherein A is as defined hereinbefore and B" represents a substituted imidazoline ring as represented in formulae (Ia/b) and (Ib/b):

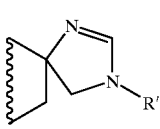  (Ia/b)

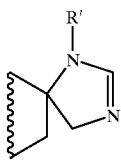

(Ib/b)

wherein R' is as defined hereinbefore,
which compounds of formulae (I/a) and (I/b) constitute the totality of the compounds of formula (I) and may be purified according to a conventional separation technique, are converted, if desired, into their addition salts with a pharmaceutically acceptable acid or base, and are separated, where appropriate, into their isomers according to a conventional separation technique.

The compounds of the invention and pharmaceutical compositions containing them have proved to be of use in the treatment of depression.

In fact, the compounds of the present invention are specific α2-adrenergic antagonists and also act as powerful inhibitors of serotonin and/or noradrenaline reuptake.

As such, they can be used therapeutically in the treatment of depression, obesity, panic attacks, anxiety, obsessive-compulsive disorders, cognitive disorders, phobias, impulsive disorders associated with the abuse of drugs and withdrawal therefrom, sexual dysfunctions and Parkinson's disease.

The present invention relates also to pharmaceutical compositions containing at least one compound of formula (I) on its own or in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, and especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, and any associated treatments, and ranges from 1 to 1000 mg per 24 hours in 1 or more administrations.

The following Examples illustrate the invention but do not limit it in any way.

EXAMPLE 1

Spiro[(1,3-diazacyclopent-1-ene)-5:2'(S)-(trans-1',2', 3',4',4'a(R),9',9'a(S),10'-octahydroanthracene)] fumarate and spiro [(1,3-diazacyclopent-1-ene)-5:2'(R)-(trans-1',2', 3',4',4'a(S),9',9'a(R),10'-octahydroanthracene)]fumarate Step 1: 7-(2-Bromobenzyl)-1,4-dioxaspiro[4.5]decan-8-one A solution of 1,4-cyclohexanedione mono-ethylene acetal (20 g, 28 mmol) in THF (360 ml) is added dropwise under nitrogen to a solution, cooled to −78° C., of 1M lithium diisopropylamide in THF (150 mmol, 150 ml), and the mixture is then allowed to return to room temperature. After stirring for 1 hour, the mixture is cooled to −78° C. and 35.2 g (141 mmol) of 2-bromobenzyl bromide are added dropwise. After stirring for 30 minutes at −78° C., the temperature of the mixture is returned to 0° C. The mixture is stirred for 3 hours at 0° C. and then hydrolysed and extracted with ether. The organic phase is washed with a saturated NaCl solution, dried over $MgSO_4$ and concentrated in vacuo. The title compound is purified by flash chromatography over a column.

Melting point: 123° C.

Step 2: 7-(2-Bromobenzyl)-8-methylene-1,4-dioxaspiro[4.5]decane

A solution of sodium tert-pentoxide (70 ml of a 1M solution), prepared for immediate use, is added to a suspension of methyl(triphenyl)phosphonium iodide (25 g, 61.8 mmol) in 50 ml of toluene, and the mixture is stirred at room temperature under nitrogen for 20 minutes. The compound obtained in Step 1 (6.70 g, 20.6 mmol) dissolved in 50 ml of toluene is added dropwise and the reaction mixture is refluxed for 3 hours. After cooling, the reaction mixture is hydrolysed with a saturated $NH_4Cl$ solution and extracted with ether. The organic phase is washed with a saturated NaCl solution, $H_2O$, dried over $MgSO_4$ and concentrated in vacuo. The title product is purified by flash chromatography over a column ($SiO_2$, toluene/cyclohexane:60/40).

Melting point: 68° C.

Step 3: 2-Dioxolane-trans-1,2,3,4,4a,9,9a,10-octahydroanthracene

A solution containing the compound obtained in Step 2 (5 g, 15.5 mmol), 510 mg (0.02 mmol) of AIBN and 6.75 g of $Bu_3SnH$ (23.2 mmol) in 750 ml of toluene is refluxed for 5 hours 30 under nitrogen. The solvent is evaporated off under reduced pressure and the resulting residue is stirred vigorously for 3 hours with a mixture of ether (120 ml) and a saturated solution of potassium fluoride (120 ml). After filtration, extraction with ether, drying over $MgSO_4$ and concentration under reduced pressure, the title product is purified by flash chromatography over a column ($SiO_2$, cyclohexane/ether:80/20).

Melting point: 71° C.

Step 4: Trans-1,2,3,4,4a,9,9a,10-octahydro-2-anthracenone

A solution of 6 g (24.6 mmol) of the acetal obtained in Step 3 in 100 ml of acetone and 25 ml of water, and 1.85 g (7.4 mmol) of pyridinium tosylate is refluxed for 4 hours. The excess solvent is evaporated off in vacuo and then 500 ml of ether are added and the reaction mixture is washed with a saturated $Na_2CO_3$ solution and a saturated NaCl solution. The organic phase is dried over $MgSO_4$ and the solvent is evaporated off under reduced pressure. The title compound is obtained after purification by flash chromatography over a column ($SiO_2$, cyclohexane/ethyl acetate:80/20).

Melting point: 99° C.

Step 5: 2-Amino-trans-1,2,3,4,4a,9,9a,10-octahydro-2-anthracenecarbonitrile 410 mg of KCN (6.3 mmol) and 340 mg of $NH_4Cl$ (6.3 mmol) are added, in succession, to a solution, stirred vigorously and maintained under nitrogen, containing 1.25 g (6.2 mmol) of the compound obtained in Step 4 in 30 ml of MeOH and 15 ml of water. After stirring for 12 hours at 20° C., the solution is diluted in $CH_2Cl_2$ and extracted with $CH_2Cl_2$. The organic phase is washed with a saturated NaCl solution, dried over $MgSO_4$ and evaporated. The residue is treated with 25 ml of a methanolic solution of ammonia (7N) and stirred in a closed system for 12 hours at 20° C. Evaporation under reduced pressure yields the title compound in pure form.

Melting point: 128° C.

Elemental microanalysis:

|  | C % | H % | N % |
|---|---|---|---|
| Theoretical | 79.61 | 8.02 | 12.38 |
| Found | 79.88 | 8.18 | 12.60 |

Step 6: 2-Aminomethyl-trans-1,2,3,4,4a,9,9a,10-octahydro-2-anthracenamine

A solution of 1.39 g (6.1 mmol) of the nitrile obtained in Step 5 in 35 ml of THF is added dropwise to a suspension of LiAlH$_4$ (350 mg, 9.2 mmol) in 35 ml of anhydrous THF at −20° C. under nitrogen. The mixture is stirred for 1 hour 30 before being hydrolysed with 2.3 ml of H$_2$O, 4.6 ml of 35% sodium hydroxide solution and 4.9 ml of water. The resulting suspension is filtered and the filtrate is evaporated to yield an oil which is subjected to flash chromatography over a column: the title compound is isolated in the form of a mixture of two diastereoisomers which are separable by HPLC (Kromasil 100, 10 C$_{18-210}$ mm—CH$_3$CN/H$_2$O/CF$_3$COOH=170/830/5).

((2S)-2-aminomethyl-trans-1,2,3,4,4a(R),9,9a(S),10-octahydro-2-anthracenamine and
(2R)-2-aminomethyl-trans-1,2,3,4,4a(S),9,9a(R),10-octahydro-2-anthracenamine)

Melting point: 123° C.

((2S)-2-aminomethyl-trans-1,2,3,4,4a(S),9,9a(R),10-octahydro-2-anthracenamine and
(2R)-2-aminomethyl-trans-1,2,3,4,4a(R),9,9a(S),10-octahydro-2-anthracenamine)

Melting point: 183° C.

Step 7: Spiro[(1,3-diazacyclopent-1-ene)-5:2'(S)-(trans-1',2',3',4',4'a(R),9',9'a(S),10'-octahydroanthracene)] fumarate
and spiro[(1,3-diazacyclopent-1-ene)-5:2'(R)-(trans-1',2',3',4',4'a(S),9',9'a(R),10'-octahydroanthracene)]fumarate A mixture of 495 mg (2.2 mmol) of (2S)-2-aminomethyl-trans-1,2,3,4,4a(R),9,9a(S),10-octahydro-2-anthracenamine and (2R)-2-aminomethyl-trans-1,2,3,4,4a(S),9,9a(R),10-octahydro-2-anthracenamine obtained in Step 6, and 258 mg (2.5 mmol) of formamidine acetate in 10 ml of EtOH is stirred at 20° C. under nitrogen for 12 hours. The solvent is removed by evaporation and the residue is taken up in 1N HCl. The acidic phase is washed with ether, rendered basic with 35% NaOH and then extracted with CH$_2$Cl$_2$. The organic phase is washed with a saturated NaCl solution, dried over MgSO$_4$ and evaporated. The solid residue is dissolved in 10 ml of EtOH and treated with a solution of fumaric acid (225 mg, 1.9 mmol) in 10 ml of EtOH. Evaporation and recrystallisation from EtOH yield the title compound in the form of a white powder.

Melting point: 233–237° C.

EXAMPLE 2

Spiro[(1,3-diazacyclopent-1-ene)-5:2'(S)-(trans-1',2',3',4',4'a(S),9',9'a(R),10'-octahydroanthracene)] fumarate
and spiro[(1,3-diazacyclopent-1-ene)-5:2'(R)-(trans-1',2',3',4',4'a(R),9',9'a(S),10'-octahydroanthracene)]fumarate The procedure is as for Step 7 of Example 1 starting from (2S)-2-aminomethyl-trans-1,2,3,4,4a(S),9,9a(R),10-octahydro-2-anthracenamine and its enantiomer.

Melting point: 215° C.

Pharmacoloical study

EXAMPLE A

Determination of the Affinity For $\alpha_2$-Adrenergic Receptors in the Rat

The affinity was determined by competition experiments with [$^3$H]-RX 821,002. The membranes are prepared from the cerebral cortex of the rat and are incubated in triplicate with 0.4 nM [$^3$H]-RX 821,002 and the product to be tested in a final volume of 1.0 ml, for 60 minutes at 22° C. The incubation buffer contains 50 nM TRIS-HCl (pH 7.5), 1 mM EDTA and 100 $\mu$M GppNHp. The non-specific binding is determined using 10 $\mu$M phentolamine.

Analysis of the data

At the end of incubation, the incubation medium is filtered through WHATMAN GF/B filters impregnated with 0.1% of polyethyleneimine, and washed three times with 5 ml of cooled buffer. The radioactivity retained on the filters is determined by liquid scintillation counting. The binding isotherms are analysed by non-linear regression.

Result

The compounds of the invention exhibit a specific $\alpha$2-adrenergic receptor antagonist activity with the compound of Example 1, for example, having a pKi of 8.0.

EXAMPLE B

Determination of the Affinity For Noradrenaline Reuptake Sites in the Rat

The affinity was determined by competition experiments with [$^3$H]-nisoxetine. The membranes are prepared from the frontal cortex of the rat and are incubated in triplicate with 2 nM [$^3$H]-nisoxetine and the product to be tested in a final volume of 0.5 ml, for 4 hours at 4° C. The incubation buffer contains 50 mM TRIS-HCl (pH 7.4), 120 mM NaCl and 5 mM KCl. The non-specific binding is determined using 10 $\mu$M desipramine.

Analysis of the data

At the end of incubation, the incubation medium is filtered through WHATMAN GF/B filters impregnated with 0.1% of polyethyleneimine, and washed three times with 5 ml of cooled buffer. The radioactivity retained on the filters is determined by liquid scintillation counting. The binding isotherms are analysed by non-linear regression.

Result

The compounds of the present invention exhibit very good affinity for the noradrenaline reuptake sites. By way of example, the pKi of the compound of Example 1 is 6.7.

EXAMPLE C

Determination of the Affinity For Serotonin Reuptake Sites in the Rat

The affinity was determined by competition experiments with [$^3$H]-paroxetine. The membranes are prepared from the frontal cortex of the rat and are incubated in triplicate with 0.25 nM [$^3$H]-paroxetine and the cold ligand in a final volume of 0.4 ml, for 2 hours at 25° C. The incubation buffer contains 50 mM TRIS-HCl (pH 7.4), 120 mM NaCl and 5 mM KCl. The non-specific binding is determined using 10 $\mu$M citalopram.

Analysis of the data

At the end of incubation, the incubation medium is filtered through WHATMAN GF/B filters impregnated with 0.1% of polyethyleneimine, and washed three times with 5 ml of cooled buffer. The radioactivity retained on the filters is determined by liquid scintillation counting. The binding isotherms are analysed by non-linear regression.

Result

The compounds of the present invention exhibit very good affinity for the serotonin reuptake sites. By way of example, the pKi of the compound of Example 1 is 7.8.

EXAMPLE D:
Pharmaceutical composition: Tablets 1000 tablets each containing 5 mg

| | |
|---|---|
| Compound of Example 1 | 5 g |
| Wheat starch | 20 g |
| Maize starch | 20 g |
| Lactose | 30 g |
| Magnesium stearate | 2 g |
| Silica | 1 g |
| Hydroxypropyl cellulose | 2 g |

We claim:

1. A compound selected from those of formula (I)

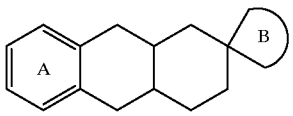

(I)

wherein:

A represents a benzene ring unsubstituted or substituted by 1 to 4 identical or different groups selected from linear or branched ($C_1$–$C_6$)alkyl, linear or branched ($C_1$–$C_6$)alkoxy, hydroxy, polyhalo-($C_1$–$C_6$)alkyl in which the alkyl moiety is linear or branched, cyano, nitro, amino, alkylamino, dialkylamino, thioalkyl, sulphonylalkyl, sulphinylalkyl, carboxy, alkoxycarbonyl, alkylcarbonyloxy, formyl, carbamoyl, carboxamide, phenyl, benzyl, and halogen, B represents an imidazoline ring as represented in formulae (Ia) or (Ib)

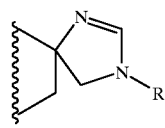

(Ia)

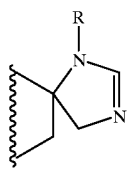

(Ib)

wherein R represents hydrogen, linear or branched ($C_1$–$C_6$) alkyl, or benzyl, it being understood that "alkyl" means linear or branched ($C_1$–$C_6$)alkyl, its tautomers, enantiomers and diastereoisomers, and addition salts thereof with a pharmaceutically-acceptable acid or base.

2. A compound of claim 1 wherein R represents hydrogen.

3. A compound of claim 1 wherein B represents a ring of formula (Ia).

4. A compound of claim 1 wherein the ring A is unsubstituted.

5. A compound of claim 1 wherein the ring A is substituted by 1 to 4 identical or different substituents selected from linear or branched ($C_1$–$C_6$)-alkyl, hydroxy, linear or branched ($C_1$–$C_6$)alkoxy, polyhalo-($C_1$–$C_6$)alkyl in which the alkyl moiety is linear or branched, and halogen.

6. A compound of claim 1 having a trans ring junction.

7. A compound of claim 1 which is spiro[(1,3-diazacyclopent-1-ene)-5:2'-(trans-1',2',3',4',4'a,9',9'a,10'-octahydroanthracene)], its tautomers, enantiomers and diastereoisomers, and addition salts thereof with a pharmaceutically-acceptable acid or base.

8. A compound of claim 1 which is a mixture of the isomers spiro[(1,3-diazacyclopent-1-ene)-5:2'(S)-(trans-1',2',3',4',4'a(R),9',9'a(S),10'-octahydroanthracene)] and spiro[(1,3-diazacyclopent-1-ene)-5:2'(R)-(trans-1',2',3',4',4'a(S),9',9'a(R),10'-octahydroanthracene)].

9. A compound of claim 1 which is a mixture of the isomers spiro[(1,3-diazacyclopent-1-ene)-5:2'(S)-(trans-1',2',3',4',4'a(R),9',9'a(R),10'-octahydroanthracene)] and spiro[(1,3-diazacyclopent-1-ene)-5:2'(R)-(trans-1',2',3',4',4'a(R),9',9'a(S),10'-octahydroanthracene)].

10. A method for treating a living body afflicted with a condition selected from depression, obesity, panic attacks, anxiety, obsessive-compulsive disorders, cognitive disorders, phobias, impulsive disorders associated with the abuse of drugs and withdrawal therefrom, sexual dysfunctions and Parkinson's disease, comprising the step of administering to the living body an amount of a compound of claim 1 which is effective for the alleviation for said condition.

11. A pharmaceutical composition useful for treating depression, comprising, as active principle, an effective amonunt of a compound as claimed in claim 1, together with one or more pharmaceutically-acceptable excipients or vehicles.

* * * * *